United States Patent [19]
Collard et al.

[11] Patent Number: 5,663,448
[45] Date of Patent: Sep. 2, 1997

[54] AROMATIC ACETYLCHOLINESTERASE INHIBITORS

[75] Inventors: Jean-Noël Collard, Illkirch Graffenstaden; Jean-Marie Hornsperger, Griesheim-près-Molsheim; Daniel Schirlin, Lampertheim, all of France

[73] Assignee: Merrell Pharmaceuticals Inc., Cincinnati, Ohio

[21] Appl. No.: 557,120

[22] PCT Filed: May 5, 1994

[86] PCT No.: PCT/US94/04957

§ 371 Date: Nov. 21, 1995

§ 102(e) Date: Nov. 21, 1995

[87] PCT Pub. No.: WO94/29255

PCT Pub. Date: Dec. 22, 1994

[30] Foreign Application Priority Data

Jun. 4, 1993 [EP] European Pat. Off. ............. 93401431

[51] Int. Cl.$^6$ .................. C07C 49/283; C07C 49/213; A61K 31/10
[52] U.S. Cl. .................... 568/335; 560/103; 564/442; 568/812
[58] Field of Search ................... 568/335, 305, 568/336, 812; 560/9, 19, 55, 103; 514/646, 688, 532, 730, 546, 689; 564/442

[56] References Cited

U.S. PATENT DOCUMENTS

| | | |
|---|---|---|
| 4,288,453 | 9/1981 | Vincent et al. . |
| 4,835,099 | 5/1989 | Mize et al. . |
| 5,017,719 | 5/1991 | Kruse et al. . |
| 5,132,328 | 7/1992 | Girodeau et al. . |
| 5,166,181 | 11/1992 | Cottens . |
| 5,214,069 | 5/1993 | Girodeau et al. . |

FOREIGN PATENT DOCUMENTS

| | | |
|---|---|---|
| 0409676 | 1/1991 | European Pat. Off. . |
| 0413667 | 2/1991 | European Pat. Off. . |
| 01163143-A | 6/1989 | Japan . |
| 02200646-A | 8/1990 | Japan . |
| 9419356 | 9/1994 | WIPO . |

OTHER PUBLICATIONS

Gelb et al., Biochemistry, vol. 24, No. 8, pp. 1813–1817 (1985).

U. Brodbeck et al., Biochimica et Biophysica Acta, 567, pp. 357–369 (1979).

K. N. Allen et al., Biochemistry 28, pp. 8466–8473 (1989).

H. K. Nair, et al., J. Am. Chem. Soc., 115, pp. 9939–9941 (1993).

R. L. Salvador et al., Tetrahedron. vol. 27, pp. 1221–1226 (1971).

R.L. Metcalf et al., J. Econ. Entomol. 58, p. 1151 (1965) (?).

A. Aberman et al., Biochimica et Biophysica Acta, 791, pp. 278–280 (1984) (?).

Bioorg. & Med. Chem Letters vol. 3 pp. 2619–2622 (1993).

*Primary Examiner*—C. Warren Ivy
*Assistant Examiner*—Jean F. Vollanu
*Attorney, Agent, or Firm*—Stephen L. Nesbitt

[57] ABSTRACT

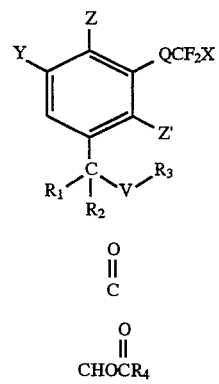

Compounds of general formula (I), stereoisomers and pharmaceutically acceptable salts thereof, wherein each of Z and Z' are independently H or F; Q is (a), CH(OH), (b); X is H, Br, Cl, F or $CF_3$; Y is H, Br, Cl, F, OH, $OR_5$, $OC(O)R_4$, $N_3$, CN, $NO_2$, $SO_3H$, $CO_2R_4$, $NH_2$, $NHR_9$, $NR_9R'_9$, $C(R_6)(R_7)$ $(V'R_8)$ or $C(O)R_7$, provided that when both Z and Z' are F, then Y is H or F; V and V' are each independently $CH_2$ or O; $R_1$ is H or $CH_3$; $R_2$, $R_9$ and $R'_9$ are each independently $(C_{1-6})$alkyl, or $R_2$ and V—$R_3$ taken together with the carbon atom to which they are attached form a 3–6 membered ring; $R_3$, $R_6$, $R_7$ and $R_8$ are each independently H, $(C_{1-6})$alkyl, or $(C_{3-6})$cycloalkyl; $R_4$ is H, $(C_{1-10})$alkyl, $(C_{0-4})$alkylene aryl or $(C_{3-8})$cycloalkyl; and $R_5$ is $(C_{1-10})$alkyl, benzyl, phenethyl or $(C_{3-6})$cycloalkyl, possess anticholinesterase activity and may be used in the treatment of Degenrativa Dementias.

13 Claims, No Drawings

AROMATIC ACETYLCHOLINESTERASE INHIBITORS

This invention relates to the use of fluorinated aromatic compounds in treating diseases associated with deficiencies of cholinergic transmission in the central nervous system and methods for their preparation.

Compounds of the present invention have the following

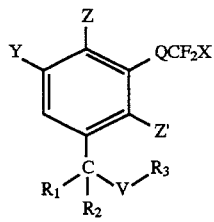    I stereoisomers and pharmaceutically acceptable salts thereof, wherein each of Z and Z' are independently H or F;

Q is

CH(OH),

X is H, Br, Cl, F or $CF_3$;

Y is H, Br, Cl, F, OH, $OR_5$, $OC(O)R_4$, $N_3$, CN, $NO_2$, $SO_3H$, $CO_2R_4$, $NH_2$, $NHR_9$, $NR_9R'_9$, $C(R_6)(R_7)(V'R_8)$ or $C(O)R_7$, provided that when both Z and Z' are F, then Y is H or F;

V and V' are each independently $CH_2$ or O;

$R_1$ is H or $CH_3$;

$R_2$, $R_9$ and $R'_9$ are each independently ($C_{1-6}$)alkyl, or $R_2$ and V—$R_3$ taken together with the carbon atom to which they are attached form a 3–6 membered ring;

$R_3$, $R_6$, $R_7$ and $R_8$ are each independently H, ($C_{1-6}$)alkyl, or ($C_{3-6}$)cycloalkyl;

$R_4$ is H, ($C_{1-10}$)alkyl, ($C_{0-4}$)alkylene aryl or ($C_{3-8}$) cycloalkyl; and $R_5$ is ($C_{1-10}$)alkyl, benzyl, phenethyl or ($C_{3-6}$)cycloalkyl.

The present invention uses compounds of Formula I to treat patients having conditions responsive to the acetylcholinesterase-inhibiting properties of the present compounds such as in the treatment of Degenerative Dementias.

The terms "($C_{1-6}$)alkyl" and "($C_{1-10}$)alkyl" mean straight or branched chain alkyl radicals containing respectively from 1 to 6 carbon atoms and from 1 to 10 carbon atoms, including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and so on. Likewise, the term "($C_{0-4}$)alkylene aryl" can mean straight or branched chain alkylene groups up to 4 carbon atoms such as ethylethylene, 2-methyltrimethylene, and so on. $C_0$ of course means no alkylene moiety attached to the aryl.

"Hydroxy($C_{1-6}$)alkyl" means a ($C_{1-6}$)alkyl group having from 1 to 3 hydroxy substituents thereon. Preferably, there is only one hydroxy substituent at the alpha position (attached to the carbon atom which is directly attached to the phenyl).

"Ts" or "tosyl" means

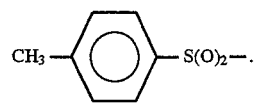

Tosyl derivatives mean

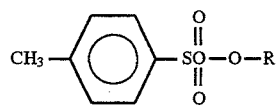

wherein R is $C_{1-6}$ alkyl.

"Aryl" includes both carbocyclic and heterocyclic moieties of which phenyl, pyridyl, indolyl, indazolyl, furyl and thienyl are of primary interest; these moieties being inclusive of their position isomers such as, for example, 2-, 3-, or 4-pyridyl, 2- or 3-furyl and thienyl, 1-, 2-, or 3-indolyl or the 1- and 3-indazolyl, as well as the dihydro and tetrahydro analogs of the furyl and thienyl moieties. Also included within the term "aryl" are such fused carbocyclic moieties as pentalenyl, indenyl, naphthalenyl, azulenyl, heptalenyl, acenaphthylenyl, fluorenyl, phenalenyl, phenanthrenyl, anthracenyl, acephenanthrylenyl, aceanthrylenyl, triphenylenyl, pyrenyl, chrysenyl and naphthacenyl. Also included within the term "aryl" are such other heterocyclic radicals as 2- or 3-benzo[b]thienyl, 2- or 3-naphtho[2,3-b] thienyl, 2- or 3-thianthrenyl, 2H-pyran-3-(or 4- or 5-)yl, 1-isobenzofuranyl, 2H-chromenyl-3-yl, 2- or 3-phenoxathiinyl, 2- or 3-pyrrolyl, 4- or 3-pyrazolyl, 2-pyrazinyl, 2-pyrimidinyl, 3-pyridazinyl, 2-indolizinyl, 1-isoindolyl, 4H-quinolizin-2-yl, 3-isoquinolyl, 2-quinolyl, 1-phthalazinyl, 1,8-naphthyridinyl, 2-quinoxalinyl, 2-quinazolinyl, 3-cinnolinyl, 2-pteridinyl, 4aH-carbazol-2-yl, 2-carbazolyl, β-carbolin-3-yl, 3-phenanthridinyl, 2-acridinyl, 2-perimidinyl, 1-phenazinyl, 3-isothiazolyl, 2-phenothiazinyl, 3-isoxazolyl, 2-phenoxazinyl, 3-isochromanyl, 7-chromanyl, 2-pyrrolin-3-yl, 2-imidazolidinyl, 2-imidazolin-4-yl, 2-pyrazolidinyl, 3-pyrazolin-3-yl, 2-piperidyl, 2-piperazinyl, 1-indolinyl, 1-isoindolinyl, 3-morpholinyl, benzo[[h]isoquinolinyl, and benzo[b] furanyl, including the position isomers thereof except that the heterocyclic moieties cannot be attached directly through their nitrogen atoms. Aryl groups can be substituted or unsubstituted with one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

When $R_2$ and V—$R_3$ are taken together, they may form a 3 membered ring which includes the carbon atom to which $R_2$ and V are attached (when $R_3$ is H). Other rings formed may have 4, 5 and 6 members to the ring. The term 3–6 membered ring refers to the number of carbon atoms, and oxygen atoms (when V is O) comprising the structure of the ring.

" Stereoisomers" for the compounds of Formula I is a general term for all isomers of individual molecules that differ only in the orientation of their atoms in space. It includes mirror image isomers (enantiomers), geometric isomers (cis/trans), and isomers of compounds with more than one chiral center that are not mirror images of one another (diastereoisomers), whichever forms are applicable to the compound.

The pharmaceutically acceptable salts of the compounds of Formula I include salts formed with non-toxic organic or inorganic acids such as, for example, from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The term "patient" refers to a warm-blooded animal, such as for example rats, mice, dogs, cats, guinea pigs, primates and humans. "Treating" a patient means to prevent or alleviate the patient's disease or condition.

The term "Degenerative Dementia" as used herein means senile dementia, presenile dementia, degenerative dementia of the Alzheimer's type (which includes Alzheimer's Disease) and other types of progressively deteriorating organic mental syndromes in which there is impairment in short-term and long-term memory. The Degenerative Dementia can be mild (impairment of work or social activities but able to live alone), moderate (some degree of supervision needed), or severe (continual supervision required).

Impairment in short-term memory is the inability to learn new information and may be demonstrated by, for example, the patient's inability to remember three objects after five minutes. Long-term memory impairment is the inability to remember information that was known in the past and may be indicated by, for example, the patients' inability to remember past personal information such as their birthplace, address, occupation, what happened yesterday, etc., or the inability to remember facts of common knowledge. There is typically impairment in abstract thinking, impairment in judgment, personality changes or other disturbances of higher cortical functions.

The preparation of the compounds of Formula I may be accomplished in a variety of methods depending upon the specific combinations of variable substituents. The following general schemes illustrate only one way these compounds may be made. Other analogous chemical reactions and procedures may be utilized which may be known to those skilled in the art.

All moieties are as previously defined unless otherwise indicated.

SCHEME A:

To make sub-generic Formula II:

SCHEME A:
To make sub-generic Formula II:

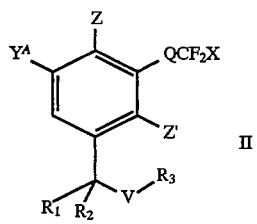

wherein
$Y^A$ is H when Z and Z' are H and when one of Z or Z' is F; and
$Y^A$ is H or F when Z and Z' are each F.

For the scheme,
W is Br when Z and Z' are H and
W is H when Z and/or Z' are F,
T is $R_3$, except for H when V is O; and
X' is H, Br, Cl, or F.

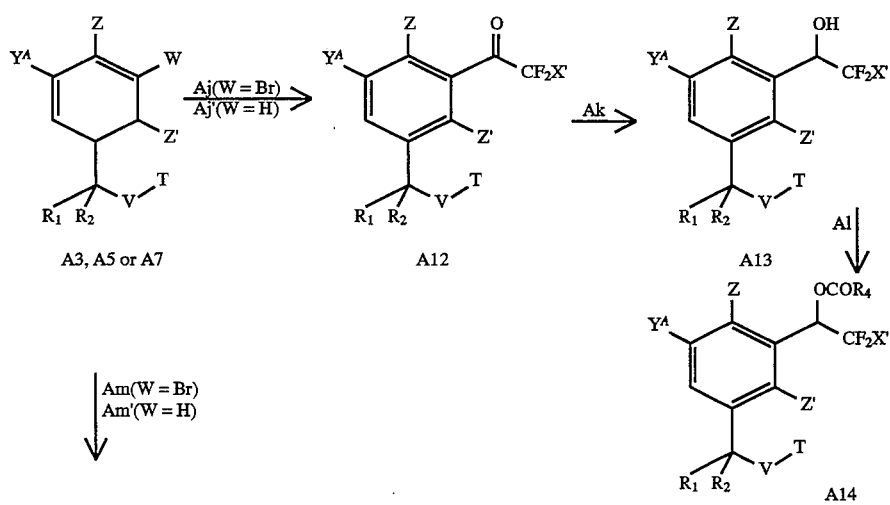

A3, A5 or A7    A12    A13

Am(W = Br)
Am'(W = H)

A14

SCHEME A:
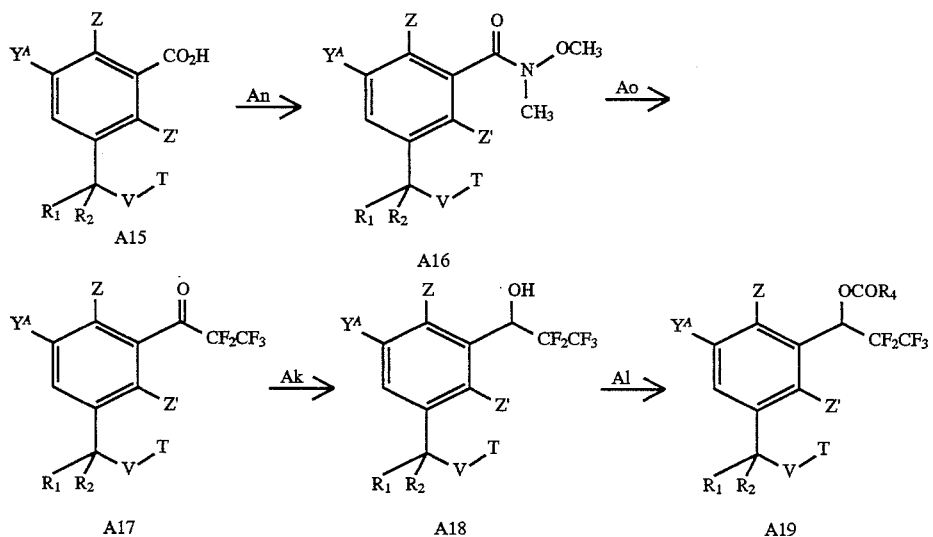
Preparation of Intermediates
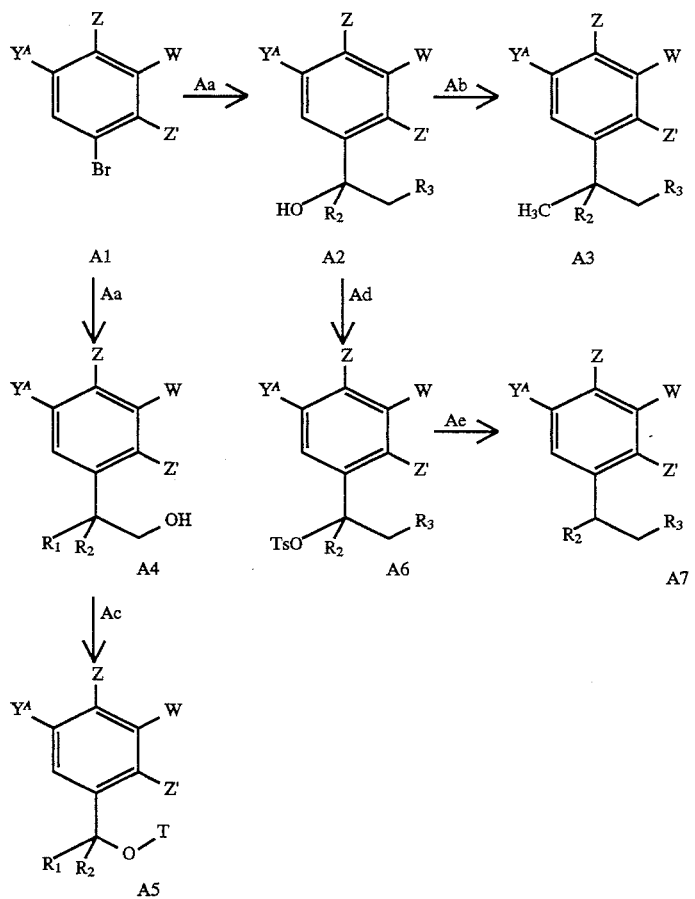

SCHEME A:

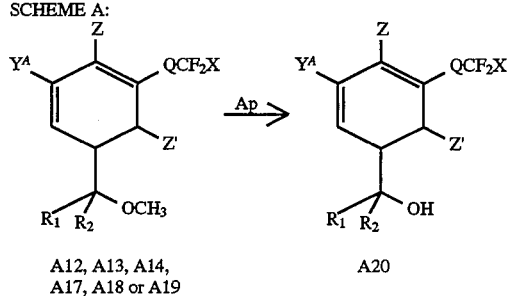

A12, A13, A14, A17, A18 or A19    A20

Starting with intermediates (A3), (A5) or (A7), when W is Br and each of Z and Z' are hydrogen, bromo derivatives (A3), (A5) or (A7) are reacted with the appropriate ester to produce (A12) which can subsequently be reduced to the alcohol (A13) and then esterified (A14). Alternatively, starting with (A3), (A5) or (A7), the acid derivatives (A15) are produced and then reacted with the appropriate agents to form hydroxamic acid derivative (A16). (A16) is reacted with a fluoroethyl anion to produce (A17). (A17) can be subsequently reduced to the alcohol derivative (A18) and esterified to produce ester derivatives (A19). Methyl ether derivatives of (A12), (A13), (A4), (A17), (A18), or (A19) can be converted to the alcohol derivative (A20).

Alternative synthesis for intermediates A3 and A7.

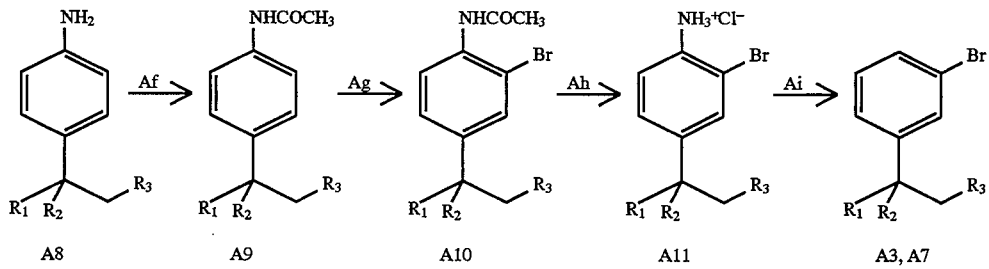

To make intermediates (A3), (A5) and (A7), the bromophenyl derivative (A1) is reacted with the appropriate aldehyde or ketone to produce the benzyl alcohol derivative (A2) or phenethyl derivative (A4) is reacted with the appropriate alkyl halide to produce the ether derivatives (A5).

Alternatively, intermediates (A3) or (A7) can be made by starting with aniline derivative (A8) and by acetylation producing (A9) which is subsequently brominated to produce (A10). The bromo derivative (A10) is deacetylated to produce (A11) and subsequently deaminated to produce (A3) (A7).

Referring to Scheme B, to make compounds of the present invention wherein Y is $NH_2$, the acid derivative (B1) is converted to the acyl azide intermediate and then to the amine (B2) by the Curtius rearrangement. The amine is protected (B3) then reacted with the appropriate ester to produce (B4) and subsequently deprotected (B5). The methyloxy derivatives of (B5) can be reduced to the alcohol (B6) and subsequently reduced to the alcohol (B7).

The protected amine ketone derivative (B4) is reduced to the alcohol (B8) which is subsequently deprotected (B9) or esterified and deprotected (B10). The methoxy derivatives of (B10) can be reduced to the alcohol (B11).

Preparation of the intermediates is shown from the bromo derivative (B13) which is alkylated with the appropriate alkylating agent and subsequently carboxylated to produce the acid derivative (B1). Alternatively, the fluoro derivative (B15) can be alkylated to produce derivative (B16) which can be carboxylated (B1).

SCHEME B:
To make sub-generic Formula III:
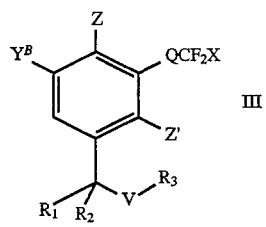
Wherein
Z and Z' are each H or F;
$Y^B = NH_2$. For the scheme
T is $R_3$, except for H when V is O.
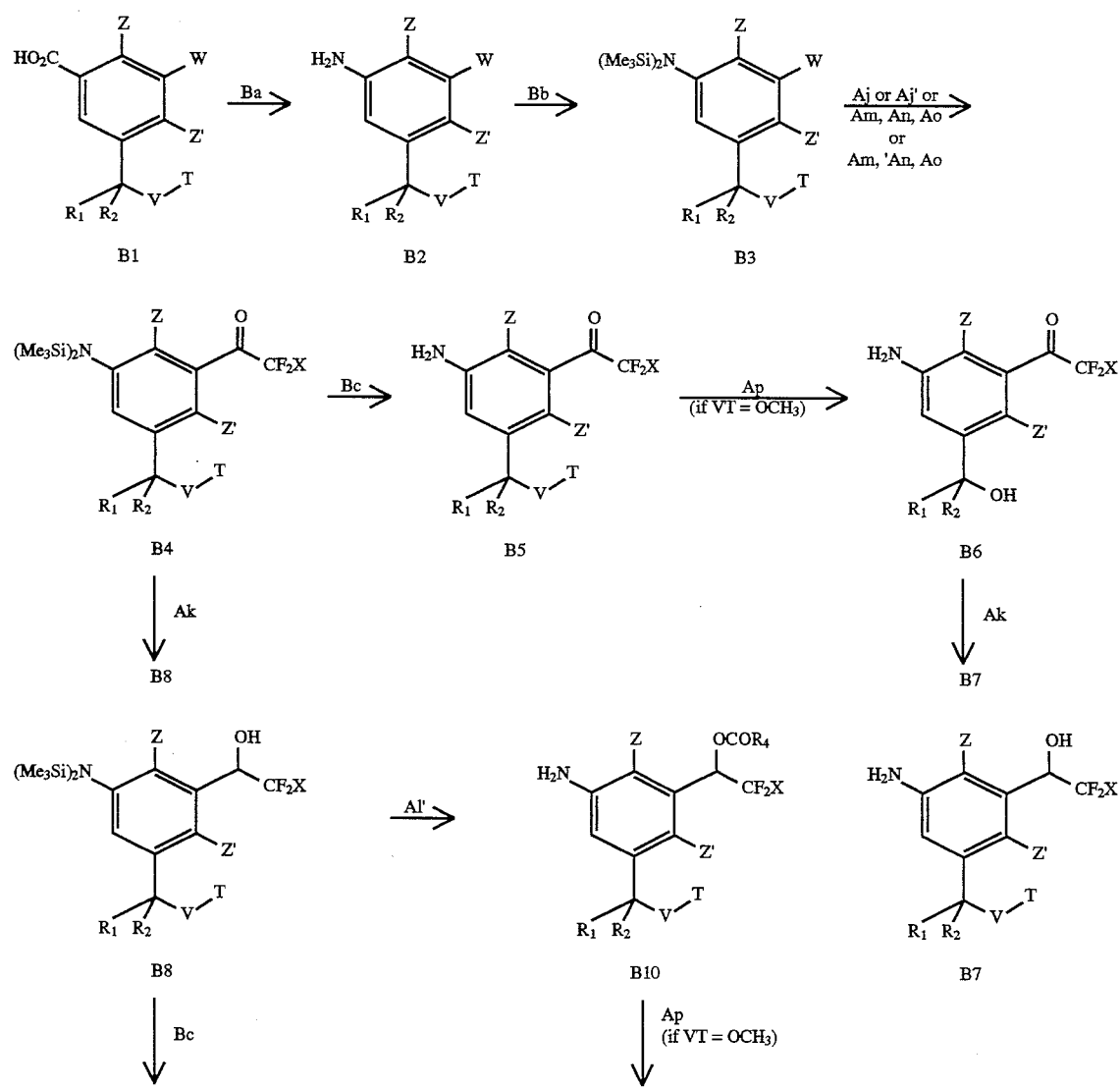

-continued
SCHEME B:
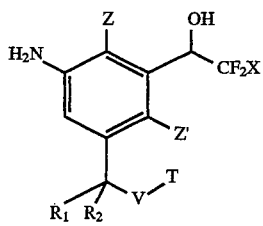
B9
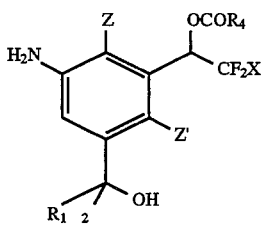
B11
The intermediates B1 are synthesized as described in the following scheme:
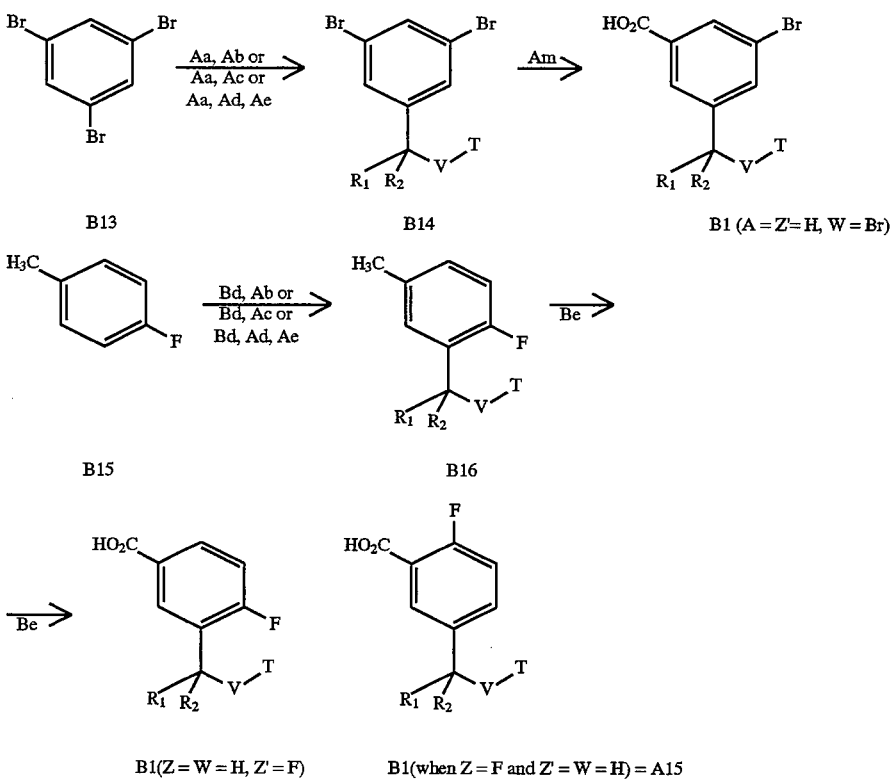
SCHEME C:
To make sub-generic Formula IV:
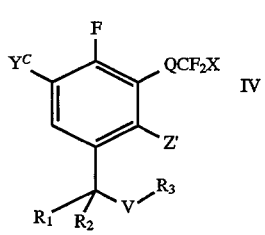
IV
wherein
Z and Z' are each H or F;
$Y^C$ is $NHR_9$ or $NR_9R'_9$. For the scheme,
T is $R_3$, except for H when V is O, and
Pg is a protecting group.
-continued
SCHEME C:
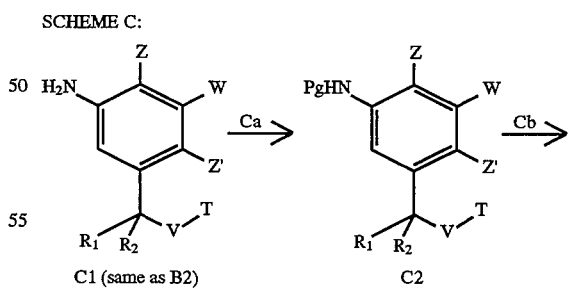
C1 (same as B2)    C2

SCHEME C:

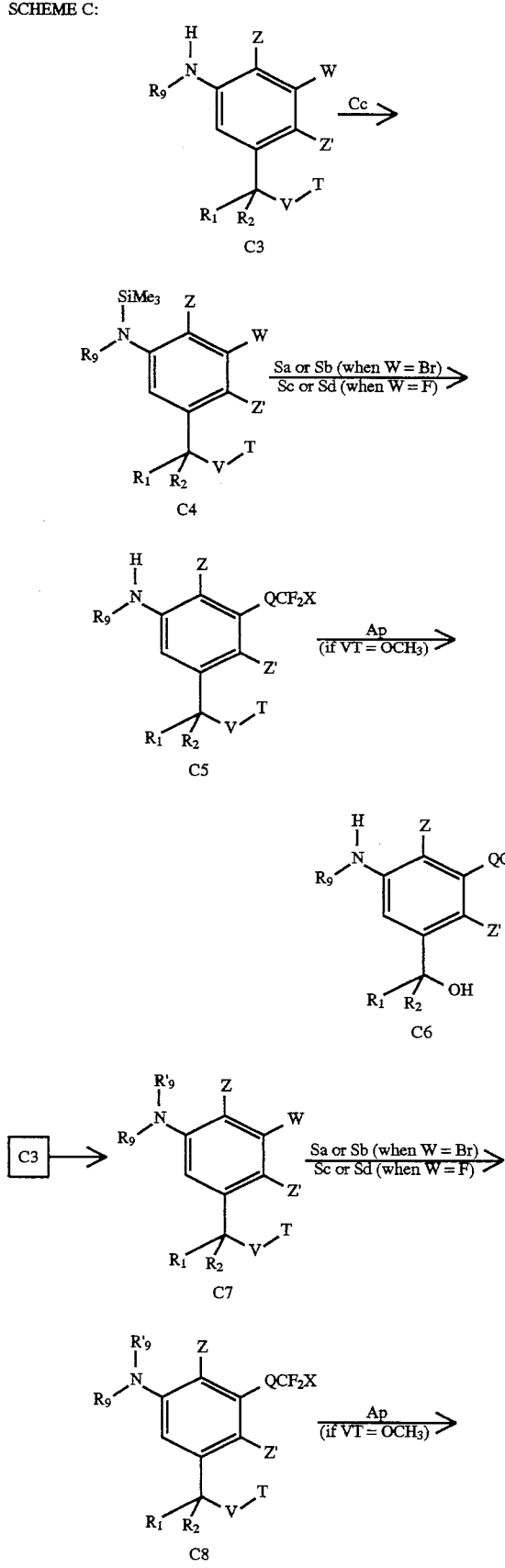

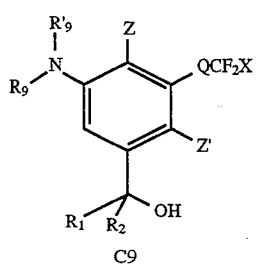

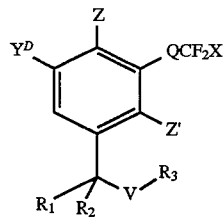

To make compounds of the present invention wherein Y is the secondary amine $NHR_9$ (Scheme C), the amine derivative (C1) is first protected with an appropriate protecting group at one position to avoid initial bis-alkylation of the amine. The unprotected site on the amine is then alkylated by reaction with the appropriate alkyl-halide reagent, followed by hydrolysis, the secondary amine (C3) is produced. An appropriate protecting group protects the secondary amine (C4) and steps previously described are performed to add the $QCF_2X$ moiety (C5). Again, when VT is methoxy, the compound can be transformed to the alcohol derivative (C6).

The secondary amine (C3) can be alkylated to produce the tertiary amine (C7). The $QCF_2X$ moiety as previously described, replaces the W moiety (C8) and the methoxy moiety (VT) can be transformed into the alcohol (C9).

SCHEME D:
To make sub-generic Formula V:

wherein

Z and Z' are each H or F;

$Y^D$ is Br, Cl, F, CN, $N_3$, $NO_2$, OH or $SO_3H$. For the scheme,

T is $R_3$ except H for when V is O.

The amino derivative (D1) of Scheme D can be treated in a variety of ways to produce the moieties of $Y^D$ as described hereafter. The ester derivative (D2) is hydrolyzed to produce the alcohol derivative (D3) which can subsequently be oxidized to the ketone (D4). If the ketone derivative (D4) has a VT moiety of methoxy, the alcohol derivative (D5) can be formed. Also, the ester moiety (D2) having a VT moiety of methoxy can form the alcohol derivative (D6) which can then be hydrolized to produce the alcohol derivative (D7).

SCHEME D (cont'd)
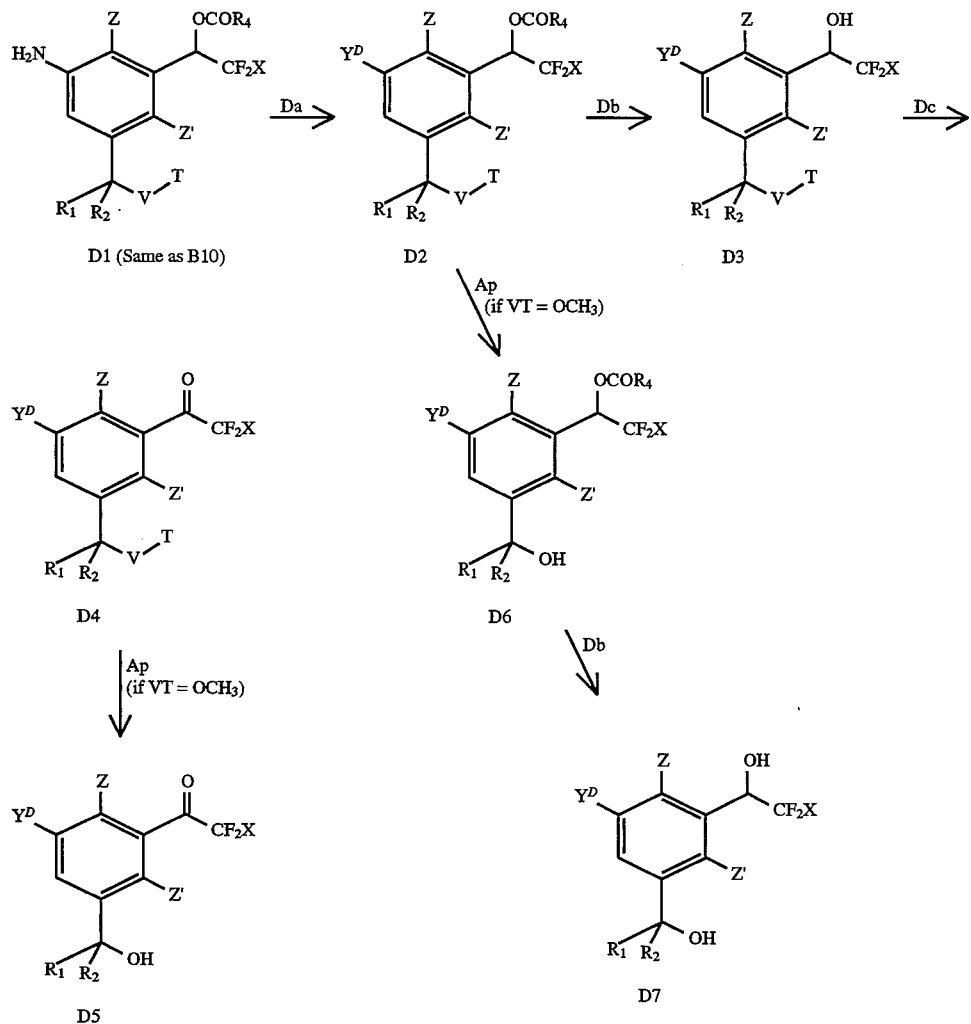
SCHEME E
Preparation of sub-generic Formula VI:
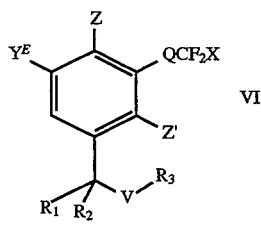
wherein
Z and Z' are each H or F;
$Y^E$ is $OR_5$ or $OCOR_4$.

-continued
SCHEME E

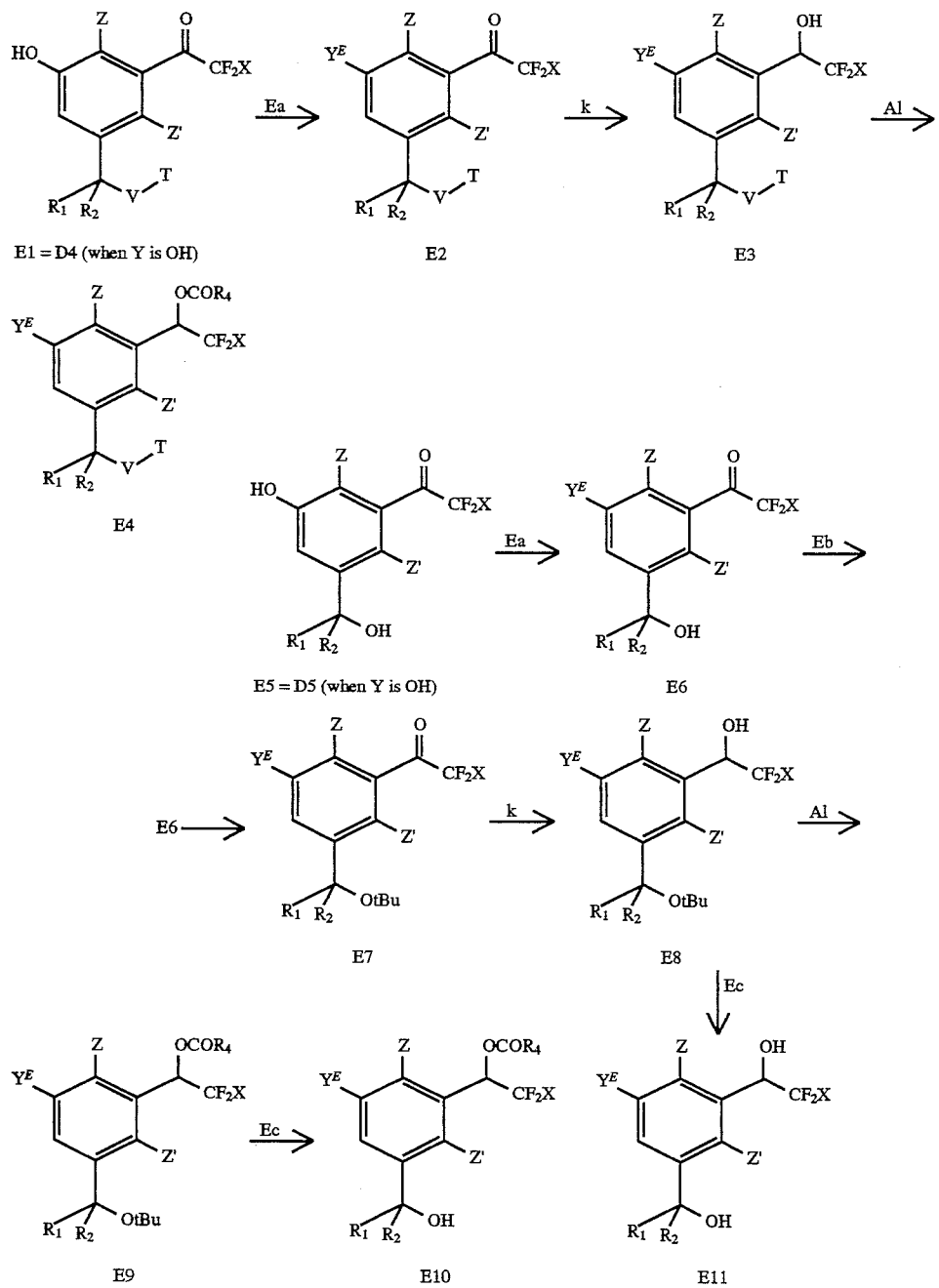

Phenol derivatives (E1) or (E5) are reacted with an appropriate alkylating agent or acyl halide agent to produce ether or ester derivatives (E2) and (E6). The ketone derivatives (E2) and (E6) are reduced to the alcohol derivatives (E3) and (E8). Prior to reduction, unprotected alcohols (E6) can be protected with, for example, t-butyl (E7) and subsequently deprotected (E10) if desired. The alcohol derivatives (E3) and (E8) can be acylated (E4) and (E9).

SCHEME F

To make sub-generic Formula VII:

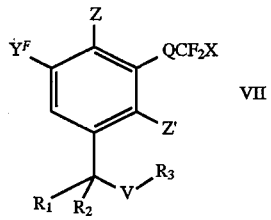

VII wherein
Z and Z' are each H or F;
$Y^F$ is $CO_2R_7$ or $C(O)R_7$.

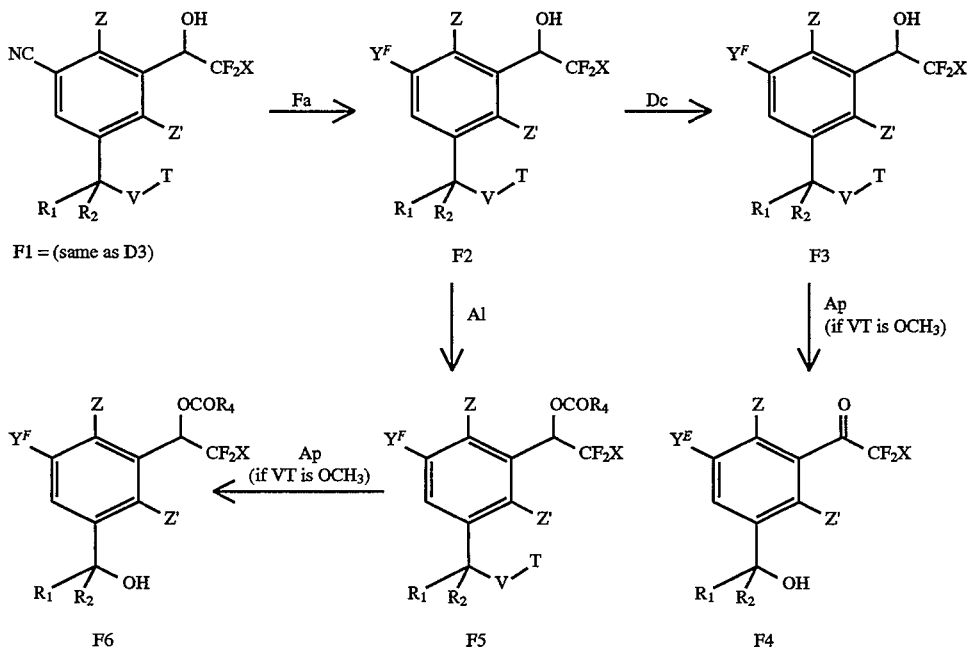

F1 = (same as D3)

Referring to Scheme F, nitrile derivative (F1) is hydrolized or alcoholized to produce acid or ester derivatives or converted to aldehyde or ketone (F2) and subsequently oxidized to produce ketone derivative (F3). The alcohol derivative (F2) can be acylated to produce ester derivatives (F5).

The alkylated derivatives G1 are made from steps previously described as shown in Scheme G.

SCHEME G

To make sub-generic Formula VIII:

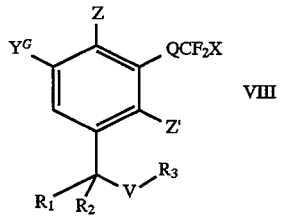

VIII wherein
Z and Z' are each H or F;
$Y^G$ is $R_6R_7CV'R_8$. For the scheme,
T is $R_3$ except H when V is O, and
T' is $R_8$ except H when V' is O.
$R_6$, $R_7$ and $R_8$ are H or $C_{1-6}$ alkyl defined in general Scheme (with $C_{3-6}$ cycloalkyl).
W is H or Br.

-continued
SCHEME G
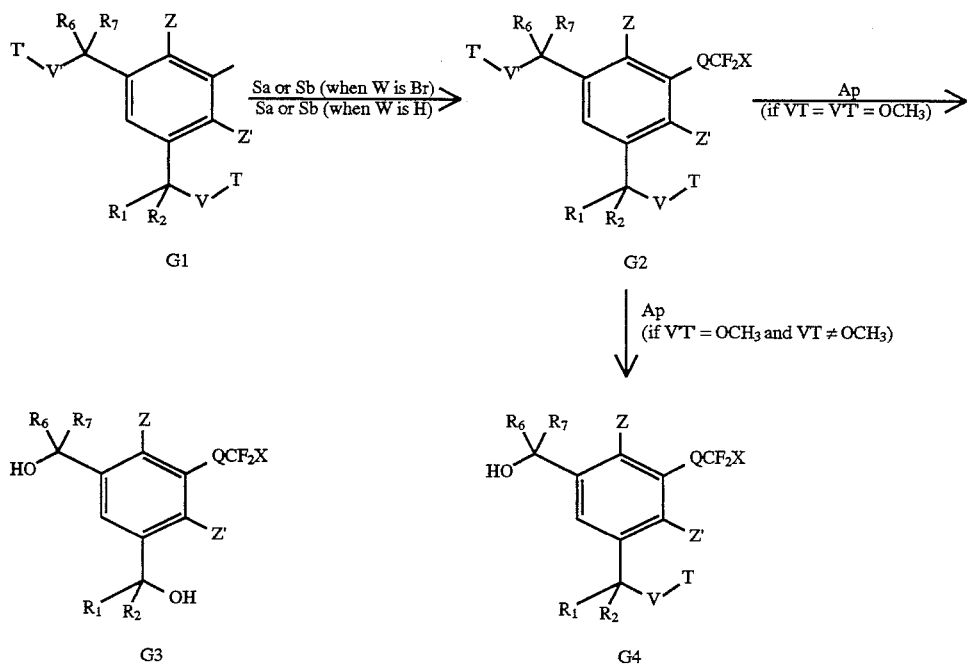
G1            G2
G3            G4
The intermediates G1 are synthesized as described in the following scheme:
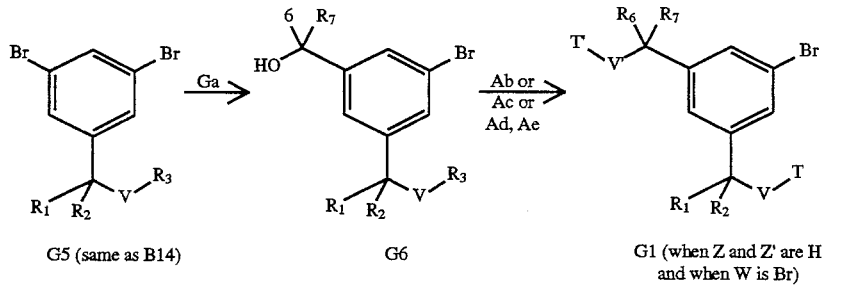
G5 (same as B14)     G6     G1 (when Z and Z' are H and when W is Br)
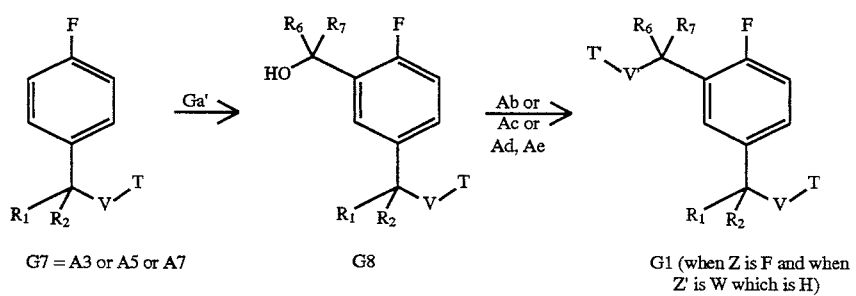
G7 = A3 or A5 or A7     G8     G1 (when Z is F and when Z' is W which is H)
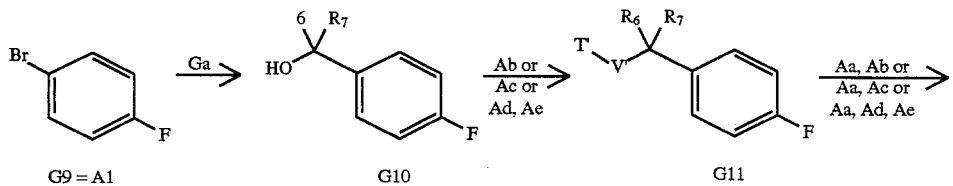
G9 = A1     G10     G11

-continued
SCHEME G

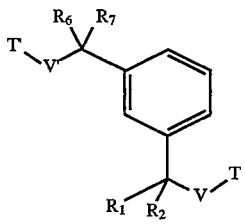

G1 (when Z' is F and Z is W, which is H)

Step Aa:
Bromophenyl derivatives A1 are converted to their lithium salt with an alkyl lithium reagent in diethyl ether or tetrahydrofuran at about −78° C. to about −60° C. for about 5–10 minutes, and then reacted at about −78° C. to about −60° C. for about one hour with an aldehyde or a ketone $R_1COR_2$ to produce benzyl alcohol derivatives A4, or reacted with a ketone $R_2COCH_2R_3$ to produce benzyl alcohol derivatives A2.

Step Ab:
Benzyl alcohol derivatives A2 are heated to about +120° C. to about +130° C. for 3–6 hours with trimethylaluminum in benzene or toluene in the presence of catalytic amount of water or acetic acid to produce alkyl derivatives A3.

Step Ac:
Benzyl alcohol derivatives A4 are converted to their sodium salt with sodium hydride in tetrahydrofuran at room temperature and those intermediates are reacted with and alkyl halide $R_3X$ ($R_3 \neq H$ and X being preferably Br or I) at room temperature for about 18 hours to produce ether derivatives A5.

Step Ad:
Benzyl alcohol derivatives A2 are reacted with paratoluenesulfonyl chloride in pyridine at 0° C. to 10° C. for 18 hours to produce tosylate derivatives A6.

Step Ae:
Tosylate derivatives A6 are reduced with lithium aluminum hydride in tetrahydrofuran at reflux or in di-n-butyl ether at about 90° C. to about 120° C. for about 3–6 hours to produce alkyl derivatives A7.

Step Af:
Aniline derivatives A8 are heated under reflux in acetic acid for about 6–8 hours in the presence of catalytic amount of zinc powder to produce N-acetyl derivatives A9.

Step Ag:
N-acetyl derivatives A9 are treated with bromine in acetic acid at about 30° C. to 40° C. for about 3–6 hours in the presence of catalytic amount of ferric chloride to produce N-acetylbromo derivatives A10.

Step Ah:
N-acetylbromo derivatives A10 are heated in a mixture of concentrated hydrochloric acid and ethanol for about one hour to produce hydrochloride salt of bromoamino derivatives A11.

Step Ai:
Hydrochloride salts of bromoamino derivatives A11 are treated with sodium nitrite in acidic medium at about 0° C. to 5° C. and then with hypophosphorus acid at about −10° C. to 0° C. for about 3 days to produce bromo derivatives A3 or A7.

Step Aj: (W=Br; Z and Z'=H; X'=H, Br, Cl or F).
The reaction involves the treatment of bromo derivatives A3, A5 or A7 with an alkyl lithium reagent at about −10° C. to 0° C. in diethyl ether or tetrahydrofuran for about 10 to 15 minutes which are then reacted with two equivalents of the appropriate ester at about −78° C. to about −60° C. for one hour (X'CF$_2$CO$_2$R, with R being preferably ethyl or methyl) or with an acid lithium salt (X'CF$_2$CO$_2$Li) at about −10° C. to 0° C. for about one hour followed by hydrolysis with aqueous ammonium chloride to produce A12.

Step Aj': (W=H, Z and/or Z'=F, X'=H, Br, Cl or F).
The reaction involves the treatment of fluoro derivatives A3, A5 or A7 with an alkyl lithium reagent at about −60° C. to −50° C. for about 5–7 hours in tetrahydrofuran and those intermediates are reacted with the appropriate ester (X'CF$_2$CO$_2$R) or acid lithium salt (X'CF$_2$CO$_2$Li) as described in Step Aj to produce A12.

Step Ak:
Ketone derivatives A12 are treated with sodium borohydride or sodium cyanoborohydride in ethanol at about 0° C. to 5° C. for one hour to produce alcohol derivatives A13.

Step Al:
Alcohol derivatives A13 are treated with an acyl chloride (ClCOR$_4$) in the presence of triethylamine in dichloromethane at about 0° C. to 5° C. for about 1–3 hours to produce ester derivatives A14.

Step Al':
Following procedure described in Step Al, ester derivatives are treated with 1N hydrochloric acid at room temperature for about 15 hours to remove N-protecting group. Free amine derivatives B10 are purified as their free bases.

Steps Am or Am':
The lithium salt intermediates prepared as described in Steps Aj or Aj' are reacted with carbon dioxide at about −60° C. to −50° C., followed by hydrolysis with aqueous ammonium chloride to produce acid derivatives A15.

Step An:
Acid derivatives A15 are reacted with isobutylchloroformate in the presence of triethyl amine or N-methyl morpholine in dichloromethane at about −30° C. to −20° C. for about 30–60 minutes to form mixed anhydrides. Then 1.5–3 equivalents of N,O-dimethylhydroxylamine hydrochloride is added and the reaction is allowed to proceed for from about 1–2 hours at about −30° C. to −20° C. and then on additional 1 to 2 hours at room temperature to produce dimethyl hydroxamic acid derivatives A16.

Step Ao:
Dimethyl hydroxamic acid derivatives A16 are converted to the pentafluoroketone derivatives A17 by treatment with a pentafluoroethyl anion generated in situ by contacting pentafluoro ethyl iodide with a methyl lithium-lithium bromide complex in diethyl ether at about −78° C. for about 5–10 minutes. Then the reaction mixture is allowed to warm to 0° C. and hydrolized with aqueous ammonium chloride.

Step Ap:
Methyl ether derivatives A12, A13, A14, A17, A18 or A19 are reacted with boron tribromide in the presence of sodium iodide and 15-crown-5 ether in dichloromethane at about −40° C. to −20° C. for about 3–6 hours followed by hydrolysis at 0° C. with aqueous sodium bicarbonate to produce benzyl alcohol derivatives A20.

Step Ba:

Carboxylic acid derivatives B1 are reacted with excess of thionyl chloride at reflux for about 1–3 hours to produce acylchloride derivatives which are reacted with sodium azide at 0° C. to 10° C. for 1–3 hours in acetone-water to produce acyl azide derivatives which are heated in benzene or toluene at about 60° C. to 100° C. for 15–60 minutes and then treated with hydrochloric acid at reflux for about 30–60 minutes to produce amine hydrochloride salt derivatives B2.

Step Bb:

Amine hydrochloride salt derivatives B2 are converted to their free amine derivatives with aqueous sodium hydroxide and then the amine moiety is bis protected with an appropriate group such as trimethylsilyl by treating the free amines with two equivalents of an alkyl lithium reagent at about −60° C. to −40° C. followed by two equivalents of chlorotrimethylsilane. Then the reaction mixture is stirred one hour at about −60° C. to −40° C. and allowed to warm to room temperature in diethyl ether or tetrahydrofuran.

Step Bc:

Bis-trimethylsilylated amine derivatives B4 are heated under reflux for 1–2 hours in aqueous methanol or ethanol to produce amine derivatives B5.

Step Bd:

Para-Fluorotoluene B15 is treated with an alkyl lithium reagent at about −60° C. to −50° C. for about 5–7 hours in tetrahydrofuran and this litio derivative is treated with an aldehyde or a ketone ($R_1COR_2$ or $R_2COCH_2R_3$) at about −78° C. to −60° C.

Step Be:

Para-Fluorotoluene derivatives B16 are heated at about 90° C. to 110° C. for about 2–3 hours with cobalt diacetate-tetrahydrate and ethyl methyl ketone in acetic acid under pressure of oxygen-butane to produce benzoic acid derivatives B1.

Step Ca:

Amine derivatives C1 are protected with an appropriate group such as tert-butyloxycarbonyl by reacting the amines with di-tert-butyldicarbonate in the presence of triethylamine in dichloromethane at room temperature for 18 hours to produce N-boc derivatives C2.

Step Cb:

N-boc derivatives C2 are reacted with sodium hydride in tetrahydrofuran for 3–6 hours at room temperature. The sodium salt intermediates are reacted with an alkyl halide reagent $R_6X$ (X being preferably Br or I) for 18 hours at room temperature followed by hydrolysis with 1N hydrochloric acid. Amine derivatives C3 are purified as their free bases after neutralization of the aqueous medium.

Step Cc:

Amine derivatives C3 are treated with an alkyl lithium reagent in tetrahydrofuran at about −60° C. to about −40° C. followed by chlorotrimethylsilane as described in Step Bd or with chlorotrimethylsilane in dichloromethane in the presence of triethylamine at room temperature for 2–3 hours to produce N-trimethylsilyl derivatives C4, as described in Step Bb.

Step Da:

This reaction involves conversion of the amine derivatives D1 to the "$Y^D$" derivatives D2 as follows:

When $Y^D$=Cl, CN, $N_3$:

The amine derivatives D1 are converted to their hydrochloride salts with aqueous hydrochloric acid and treated with sodium nitrite at about 0° C. to 5°0 C. to produce diazonium salts which are heated with cuprous chloride from 20° C. to 60° C. to produce chloro derivatives or treated with cuprous cyanide at about 0° C. to 30° C. to produce nitrile derivatives or treated with sodium azide at about 0° C. to 10° C. to produce azide derivatives.

When $Y^D$=F or $NO_2$:

The amine derivatives D1 are dissolved with aqueous hydrochloric acid and treated with sodium nitrite at about 0° C. to 5° C. followed by aqueous fluoroboric acid at about 0° C. to 5° C. The fluoroborate diazonium salt is filtered, dried and is heated gently until decomposition begins and proceeds smoothly to produce fluoro derivatives. To produce nitro derivatives, fluoroborate diazonium salts are added to a mixture of aqueous sodium nitrite and copper powder at about 0° C. to 5° C.

When $Y^D$=Br:

The amine derivatives D1 are dissolved in aqueous hydrobromic acid, treated with sodium nitrite at about 0° C. to 10° C. and then with copper powder at about 20° C. to 100° C. to produce bromide derivatives.

When $Y^D$=OH:

The amine derivatives D1 are dissolved in aqueous sulfuric acid, treated with sodium nitrite at about 0° C. to 5° C. to produce diazonium salt. The diazonium salt solution is slowly added to a boiling aqueous sulfuric acid solution to produce phenol derivatives.

When $Y^D$=$SO_3H$:

The amine derivatives D1 are dissolved in concentrated hydrochloric acid and treated with sodium nitrite at about 0° C. to 5° C. Then the diazonium salt is added to a mixture of sulfur dioxide, copper chloride and potassium chloride in dioxane-benzene. The resulting mixture is heated at about 40° C. to 60° C. for about 1 to 3 hours to produce sulfonyl chloride derivatives which are heated under reflux in aqueous sodium carbonate for 1–3 hours to produce sulfonic acid derivatives.

Step Db:

Ester derivatives D2 or D6 are hydrolized with lithium hydroxide in aqueous dimethoxyethane at room temperature for about 1 to 6 hours to produce alcohol derivatives D3 or D7.

Step Dc:

Alcohol derivatives D3 are oxidized with pyridinium dichromate, or with Dess-Martin periodinane oxidant in dichloromethane at about 0° C. to 25° C. for 18 hours or by Swern reaction to produce ketone derivatives D4.

Step Ea ($Y^E$=$OR_5$):

Phenol derivatives E1 or E5 are converted to their sodium or potassium salts with sodium or potassium carbonate in water or acetone at about room temperature and reacted with an alkyl halide reagent $R_5X$ (X being preferably Br or I) at room temperature for 18 hours to produce ether derivatives E2 or E6.

Step Eb:

Benzyl alcohol derivatives E6 dissolved in dichloromethane or chloroform are treated with isobutylene in phosphoric acid-boron trifluoride etherate for about 1 to 3 hours at about −78° C. to −60° C. then 18 hours at room temperature or with tert-butyl-2,2,2-trichloroacetamidate in the presence of a catalytic amount of boron trifluoride etherate in cyclohexane or in a mixture of cyclohexane-dichloromethane at room temperature for about 18–24 hours to produce tert-butyl ether derivatives E7.

Step Ec:

tert-Butyl ether derivatives E8 or E9 are treated with trifluoroacetic acid at about 0° C. to 20° C. for about 18 hours to produce benzyl alcohol derivatives E10 or E11.

Step Fa (when $Y^F=CO_2R_7$):

Nitrile derivatives F1 are heated under reflux for 1–3 hours in aqueous hydrochloric acid to produce acid derivatives ($R_4=H$) or heated under reflux for about 3–6 hours with 95% alcohol $R_4OH$ ($R_4 \neq H$) saturated with dry hydrochloric acid or with concentrated sulfuric acid to produce ester derivatives.

Step Fa (when $Y^F=COR_6$:

Nitrile derivatives F1 are treated with anhydrous stannous chloride and hydrogen chloride in diethyl ether or tetrahydrofuran at about 0° C. to 20° C. for about 18 hours followed by hydrolysis with cold water to produce aldehyde derivatives ($R_6=H$) or nitrile derivatives are treated with a Grignard reagent $R_6MgX$ (X being preferably Br or I) in diethyl ether or tetrahydrofuran at about 20° C. to 60° C. for 1–3 hours followed by hydrolysis with aqueous hydrochloric acid to produce ketone derivatives.

Step Ga:

Dibromo derivatives G5 are treated with an alkyl lithium reagent at about −30° C. to 0° C. in diethyl ether or tetrahydrofuran for about 10–20 minutes and those lithium derivative intermediates with paraformaldehyde or with an aldehyde or with a ketone ($R_6COR_7$) at about −78° C. to about −60° C. for about one hour to produce benzyl alcohol derivatives G6.

Step Ga':

Fluoro derivatives G7 are treated with an alkyl lithium reagent at about −60° C. to −40° C. in diethyl ether or tetrahydrofuran for 5–7 hours and those lithium derivative intermediates are reacted with paraformaldehyde or with an aldehyde or with a ketone ($R_6COR7$) at about −78° C. to −60° C. for about one hour to produce benzyl alcohol derivatives G10.

Step Sa=steps Aj+Ak+Al; Step Sb=Steps Am+An+Ao+Ak+Al; Step Sc=steps Aj'+Ak+Al; and Step Sd=steps Am'+An+Ao+Al.

For the cyclic derivatives, when $R_2$ and V—$R_3$, together with the carbon atom to which $R_2$ and V are attached, form a 3–6 membered ring:

When V=$CH_2$ and $R_1$=H, $CH_3$.

Bromobenzene derivatives A1 are reacted with the appropriate cyclic ketone $(CH_2)_{2-5}C(O)$ as described in Step Aa and then by using Step Ab or Steps Ad and Ae cycloalkyl derivatives are produced.

When V=O and $R_1$=$CH_3$.

Bromobenzene derivatives A1 are reacted with an halogeno alkyl methyl ketone X-$(CH_2)_{1-4}C(O)CH_3$ (X being Br or Cl) as described in Step Aa and then the intermediates are heated under reflux for 18 hours to produce cycloalkylether derivatives.

When V=O and $R_1$=H.

Bromobenzene derivatives A1 are reacted with a halogenoalkylaldehyde X-$(CH_2)_{1-4}CHO$ (X being Br or Cl) as described above. Those halogenoalkyladehydes are prepared by oxidation of the corresponding alcohols with a mixture of dimethylsulfoxide, pyridine, trifluoracetic acid and dicyclohexyl carbodiimide in benzene or toluene at room temperature for 18 hours.

Having generically described the methods for the preparation of the compounds of this invention, the following specific examples illustrate the chemistry and techniques by which the synthesis may be effected.

EXAMPLE 1

2,2,2-Trifluoro-1-(3-tert-butylphenyl) ethanone

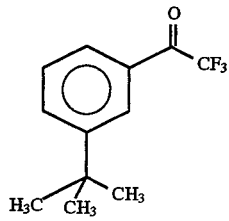

STEP A:

N-Acetyl-4-tert-butyl aniline

A mixture of 20 g (134 mmol) of 4-tert-butyl aniline and 0.044 g (0.67 mmol) of zinc powder in 20 ml acetic acid is heated under reflux for 7 hours. Then the crude product is poured into 350 ml of ice water and filtered. Recrystallization in ethanol-water affords 20.83 g (81%) of the title compound.

STEP B:

N-Acetyl-2-bromo-4-tert-butyl aniline

To a solution of 20.80 g (108.7 mmol) of N-acetyl-4-tert-butyl aniline and 0.33 g (2 mmol) of ferric chloride in 70 ml of acetic acid is added dropwise 17.9 g (112 mmol) of bromine while the temperature is kept between 30° C. and 40° C. Then the reaction mixture is stirred 4 hours and poured into 500 ml of ice water. The precipitate is filtered off, washed with water and recrystallized from 70% ethanol. Thus is obtained 24.33 g (83%) of title compound.

STEP C:

2-Bromo-4-tert-butyl aniline hydrochloride

A solution of 24.33 g (90 mmol) of N-acetyl-2-bromo-4-tert-butyl aniline in 73.5 ml of 95% ethanol and 46 ml of concentrated hydrochloric acid is heated under reflux one hour. Then the mixture is cooled and the product is filtered, washed with cold 95% ethanol and dried. The yield of title compound is 21.75 g (91%).

STEP D: 3-Bromo-tert-butyl benzene

To a solution of 9.34 g (35.3 mmol) of 2-bromo-4-tert-butyl hydrochloride in 51 ml of acetic acid, 34 ml of water and 12 ml of concentrated hydrochloric acid at 0° C. is added dropwise 2.63 g (38.1 mmol) of sodium nitrite in 15 ml of water while temperature is kept between 0° C. and 5° C. Then the solution is poured into 40 ml of 50% hypophosphorus acid and 20 ml of water at 0° C. and the total solution is stirred 3 days at 0° C. The colored oil formed is removed by use of separatory funnel, dissolved in ethyl acetate, washed with water and brine and dried over magnesium sulfate. Ethyl acetate is removed and title compound is purified by distillation. The yield of 3-bromo-tert-butyl benzene is 6.01 g (80%); b.p.: 108° C./16 mmHg.

STEP E:

2,2,2-Trifluoro-1-(3-tert-butyl)phenyl ethanone

To a solution of 5.85 g (27.5 mmol) of 3-bromo-tert-butyl benzene in 55 ml of diethyl ether at 0° C. is added dropwise 18.5 ml of 1.5M n-butyllithium in hexane. The reaction mixture is stirred 10 minutes at 0° C. and cooled to −78° C. Then 11.71 g (82.5 mmol) of ethyl trifluoroacetate is added dropwise and the reaction mixture is stirred one hour at −78°

C. Cooling bath is removed and when the temperature rised to 0° C., 100 ml of 3N hydrochloric acid is added. The organic layer is separated, washed with water and brine, dried over magnesium sulfate and concentrated. Chromatography on silica gel (2% of ethyl acetate in petroleum ether) followed by distillation afforded 0.73 g of title compound ( 11.5% ); b.p.: 142° C./22 mmHg.

EXAMPLE 2

2,2,2-Trifluoro-1-(3-tert-butyl)phenyl ethanol

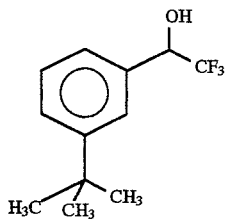

To a solution of 0.46 g (2 mmol) of 2,2,2-trifluoro-1-(3-tert-butyl)phenyl ethanone in 10 ml of ethanol at 0° C. is added 0.08 g (2.1 mmol) of sodium borohydride. The reaction mixture is stirred one hour at room temperature, cooled to 0° C. and hydrolized with 1.28 g (24 mmol) of ammonium chloride in 20 ml of water. Ethanol is removed under reduced pressure and crude product is extracted with ethyl acetate. The organic layer is washed with brine, dried over magnesium sulfate and concentrated. Title compound is purified by chromatography on silica gel (5% of ethyl acetate in petroleum ether).

EXAMPLE 3

[2,2,2-Trifluoro-1-(3-tert-butyl)phenyl]ethyl acetate

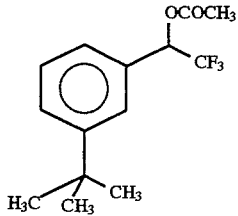

To a solution of 0.30 g (1.3 mmol) of 2,2,2-trifluoro-1-(3-tert-butyl)phenyl ethanol and 0.13 g (1.3 mmol) of triethylamine in 5 ml of dichloromethane at 0° C. is added dropwise 0.10 g (1.3 mmol) of acetyl chloride in 2 ml of dichloromethane. The reaction mixture is stirred 3 hours at room temperature, washed with water, brine, dried over magnesium sulfate and concentrated. Title compound is purified by chromatography on silica gel (2% of ethyl acetate in petroleum ether).

EXAMPLE 4

2,2,2-Trifluoro-1-[3-(2-propyl methyl ether)]phenyl ethanone

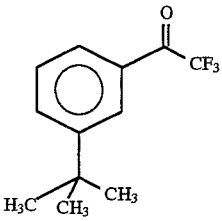

STEP A:

1-Bromo-3-(2-propanol)benzene

To a solution of 5.90 g (25 mmol) of 1,3-dibromobenzene in 25 ml of tetrahydrofuran at −30° C. is added dropwise 17 ml (25.5 mmol) of 1.5M n-butyllithium in hexane. Then the reaction mixture is stirred 10 minutes at −30° C. and cooled to −78° C. To the solution is added dropwise 1.74 g (30 mmol) of acetone in 10 ml of tetrahydrofuran and the reaction mixture is stirred 30 minutes at −78° C. Cooling bath is removed and when the temperature rises to 0° C., 50 ml of 1N hydrochloric acid is added dropwise, followed by 50 ml of ethyl acetate. The organic layer is removed, washed with water, brine, dried over magnesium sulfate and concentrated. Chromatography on silica gel (5% of ethyl acetate in petroleum ether) affords 2.72 g (51%) of title compound.

STEP B:

1-Bromo-3-(2-propylmethylether)benzene

A solution of 2.72 g (12.65 mmol) of 1-bromo-3-(2-propanol)benzene in 15 ml of tetrahydrofuran is added dropwise in 0.51 g (12.70 mmol) of 60% sodium hydride in 15 ml of tetrahydrofuran at 0° C. Then the reaction mixture is stirred 3 hours at room temperature and 2.15 g (15.15 mmol) of methyl iodide in 7 ml of tetrahydrofuran is added dropwise. The resulting mixture is stirred at room temperature for 18 hours, treated with 30 ml of 1N hydrochloride and extracted with 30 ml of ethyl acetate. The organic layer is separated, washed with water, brine, dried over magnesium sulfate and concentrated. Chromatography on silica gel (2% of ethyl acetate in petroleum ether) affords 1.62 g (56%) of title compound.

STEP C:

2,2,2-Trifluoro-1-[3-(2-propyl methyl ether)]phenyl ethanone

To a solution of 0.81 g (3.5 mmol) of 1-bromo-3-(2-propylmethylether)benzene in 5 ml of tetrahydrofuran at −40° C. is added dropwise 2.4 ml (3.6 mmol) of 1.5M n-butyl-lithium in hexane. Then the reaction mixture is stirred 30 minutes at −40° C., cooled to −78° C. and 0.99 g (7 mmol) of ethyl acetate is added dropwise. The resulting reaction mixture is stirred 30 minutes at −78° C. and cooling bath is removed. At 0° C. 10.5 ml of 1N hydrochloric acid is added followed by 10 ml of ethyl acetate. The organic layer is removed, washed with water and brine, dried over magnesium sulfate and concentrated. Chromatography on silica gel (10% of ethyl acetate in petroleum ether) affords 0.39 g (45%) of the title compound.

EXAMPLE 5

2,2,2-Trifluoro-1-[3-(2-propanol)]phenyl ethanone

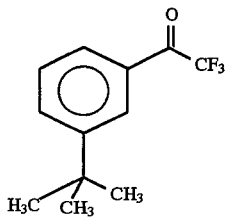

To a mixture of 0.30 g (1.2 mmol) of 2,2,2-trifluoro-1-[3-(2-propylmethylether)]phenyl ethanone and 0.72 g (4.8 mmol) of sodium iodide in 5 ml of dichloromethane at −40° C. is added dropwise 1.06 g (4.8 mmol) of 15-crown-5 in 10 ml of dichloromethane. The reaction mixture is stirred 10 minutes at −40° C. and 3.6 ml of a 1.0M solution of borontribromide in dichloromethane is added dropwise. Then the resulting reaction mixture is stirred 3 hours at −40° C., allowed to warm to 0° C., and hydrolized with 10 ml of saturated aqueous sodium bicarbonate. The organic layer is separated, washed with water and brine, dried over magnesium sulfate and concentrated. Chromatography on silica gel (20% of ethyl acetate in petroleum ether) affords title compound.

EXAMPLE 6

2,2,2-Trifluoro-1-[2-fluoro-5-(1-diethylether)]phenyl ethanone

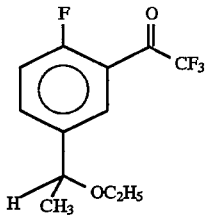

STEP A:

4-(1-Diethylether)-1-fluorobenzene

A solution of 1.40 g (10 mmol) of 1-(4-fluorophenyl)ethanol in 10 ml of tetrahydrofuran is added dropwise on 0.40 g (10 mmol) of 60% sodium hydride in 10 ml of tetrahydrofuran at 0° C. Then the reaction mixture is stirred 3 hours at room temperature and 1.56 g (10 mmol) of ethyl iodide in 10 ml of tetrahydrofuran is added dropwise. The resulting mixture is stirred at room temperature for 18 hours, treated with 20 ml of 1N hydrochloric acid and extracted with 30 ml of ethyl acetate. The organic layer is separated, washed with water, brine, dried over magnesium sulfate and concentrated. Chromatography on silica gel (2% of ethyl acetate in petroleum ether) affords title compound.

STEP B:

2,2,2-Trifluoro-1-[3-(2-diethylether)-6-fluoro]phenyl ethanone

To a solution of 0.84 g (5 mmol) of 4-(1-diethylether)-1-fluorobenzene in 10 ml of tetrahydrofuran at −50° C. is added dropwise 3.33 ml (5 mmol) of 1.5M n-butyllithium in hexane. The reaction mixture is stirred 6 hours at −50° C. and cooled to −78° C. Then 1.42 g (10 mmol) of ethyl trifluoro acetate in 5 ml of tetrahydrofuran is added dropwise and the mixture is stirred 30 minutes at −78° C. Cooling bath is removed and at 0° C. 15 ml of 1N hydrochloric acid is added dropwise followed by 20 ml of ethyl acetate. The organic layer is removed, washed with water and brine, dried over magnesium sulfate and concentrated. Chromatography on silica gel (10% of ethyl acetate in petroleum ether) affords title compound.

EXAMPLE 7

2,2,2-Trifluoro-1-(2-fluoro-3-isopropyl)phenyl ethanone

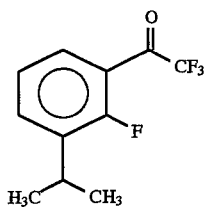

STEP A:

2-(2-Fluoro)phenyl-2-propanol

To a solution of 20 ml (30 mmol) of 1.5M n-butyllithium in hexane diluted with 10 ml of tetrahydrofuran at −78° C. is added dropwise a solution of 5.25 g (30 mmol) of 2-bromo-1-fluorobenzene in 30 ml of tetrahydrofuran. 5 minutes later a solution of 2.03 g (35 mmol) of acetone in 10 ml of tetrahydrofuran is added dropwise. Cooling bath is removed and at 0° C. 30 ml of 3N hydrochloric acid is added dropwise. The reaction mixture is extracted with 60 ml of ethyl acetate and the organic layer is washed with water and brine, dried over magnesium sulfate and concentrated. Title compound is purified by distillation.

STEP B:

2-(2-Fluoro)phenyl-2-propyl p-toluenesulfonate

To a solution of 2.08 g (20 mmol) of 2-(2-fluoro)phenyl-2-propanol in 10 ml of pyridine, cooled to 0° C., is added dropwise 4.20 g (22 mmol) of p-toluenesulfonylchloride in 5 ml of pyridine, and the resulting mixture is stirred at 0° C. for 18 hours. The reaction mixture is poured into 100 ml of water and extracted with 50 ml of ethyl acetate. The organic layer is separated, washed with water and brine, dried over magnesium sulfate and concentrated. Recrystallization from hexane affords title compound.

STEP C:

2-Isopropyl-1-fluorobenzene

To a solution of 4.62 g (15 mmol) of 2-(2-fluoro)phenyl-2-propyl p-toluenesulfonate in 150 ml of di-n-butyl ether is added dropwise 18 ml (18 mmol) of 1M lithium aluminum hydride in tetrahydrofuran. Then the reaction mixture is stirred at 100° C. for 4 hours, cooled to 0° C. and 2 ml of water is added dropwise. The resulting mixture is filtered, washed with water and brine, dried over magnesium sulfate and concentrated. Title compound is purified by distillation.

STEP D:

2,2,2-Trifluoro-1-(2-fluoro-3-isopropyl)phenyl ethanone

Title compound is prepared as described in Step B of Example 6 and purified by chromatography on silica gel (10% ethyl acetate in petroleum ether) followed by distillation.

EXAMPLE 8

2,2,2-Trifluoro-1-[2-fluoro-3-(N,N-dimethylamino)-5-(1-diethylether)]phenyl ethanone

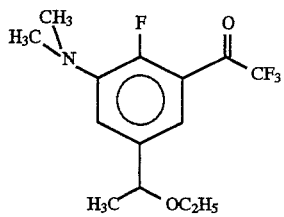

STEP A:

2-Fluoro-5-(1-diethylether) benzoic acid

To a solution of 6.72 g (40 mmol) of 4-(1-diethylether)-1-fluorobenzene in 60 ml of tetrahydrofuran at −50° C. is added dropwise 26.7 ml (40 mmol) of 1.5M n-butyllithium in hexane. The reaction mixture is stirred 6 hours at −50° C. and treated with excess of carbon dioxide. Then cooling bath is removed and, at 0° C., 60 ml of water is added dropwise. Tetrahydrofuran is removed under reduced pressure and the aqueous solution is extracted twice with 30 ml of n-hexane. The aqueous layer is acidified with 20 ml of 4N hydrochloric acid, extracted twice with 50 ml of ethyl acetate. The organic layers are combined, washed with brine, dried over magnesium sulfate and concentrated. Title compound is recrystallized from isopropanol.

STEP B:

N-(tert-Butoxycarbonyl)-[2-fluoro-5-(1-diethylether]aniline

A mixture of 6.36 g (30 mmol) of 2-fluoro-5-(1-diethylether)benzoic acid and 5.35 g (45 mmol) of thionyl chloride is heated 2 hours at 60° C. Then gases and excess of thionyl chloride are removed under reduced pressure. The crude product is dissolved in 20 ml of acetone and 2.60 g (40 mmol) of sodium azide in 20 ml of water is added dropwise. The reaction mixture is stirred 1 hour at 0° C. and acetone is removed under reduced pressure. To the aqueous mixture is added 40 ml of ethyl acetate, then the organic layer is separated, washed with brine and dried over magnesium sulfate. Ethyl acetate is removed under reduced pressure and the crude product is dissolved in 40 ml of benzene and heated under reflux for 1 hour. Then the reaction mixture is cooled to 0° C. and 20 ml of concentrated hydrochloric acid is added. The resulting mixture is heated under reflux for 30 minutes and cooled. Benzene is removed and 100 ml of 3N sodium hydroxide solution is added to the aqueous mixture, followed by 100 ml of ethyl acetate. The organic layer is separated, washed with brine, dried over magnesium sulfate and concentrated. The crude material is dissolved in 80 ml of dichloromethane and 4.04 g (40 mmol) of triethylamine was added. To the resulting mixture is added dropwise 9.60 g (44 mmol) of di-tert-butyl dicarbonate in 20 ml of dichloromethane and the reaction mixture is stirred at room temperature for 18 hours. Then dichloromethane and triethylamine are removed under reduced pressure and title compound is purified by chromatography on silica gel (10% of ethyl acetate in petroleum ether).

STEP C:

N-Methyl-[2-fluoro-5-(1-diethylether)]aniline

A solution of 4.23 g (15 mmol) of N-(tert-butoxycarbonyl)-[2-fluoro-5-(1-diethylether)]aniline in 15 ml of tetrahydrofuran is added dropwise to 0.60 g (15 mmol) of 60% sodium hydride in 15 ml of tetrahydrofuran at 0° C. Then the reaction mixture is stirred 3 hours at room temperature and 2.55 g (19 mmol) of methyl iodide in 15 ml of tetrahydrofuran is added dropwise. The resulting mixture is stirred at room temperature for 18 hours, cooled to 0° C. and 15 ml of concentrated hydrochloric acid is added dropwise. Stirring is continued for 3 hours at room temperature and tetrahydrofuran is removed under reduced pressure. To the aqueous medium, 70 ml of 3N sodium hydroxide solution is added dropwise, followed by 60 ml of ethyl acetate. The organic layer is separated, washed with brine, dried over magnesium sulfate and concentrated. The crude product is dissolved in 15 ml of diethyl ether and treated with 15 ml of a saturated solution of hydrochloric acid in diethyl ether. The hydrochloride salt is filtered and recrystallized from isopropanol-diethyl ether. The resulting salt is dissolved in 10 ml of water and to the aqueous medium is added 10 ml of a saturated sodium carbonate solution followed by 20 ml of ethyl acetate. The organic layer is separated, washed with brine, dried over magnesium sulfate and concentrated to afford the title compound.

STEP D:

N,N-Dimethyl-[2-fluoro-5-(1-diethylether]aniline

Title compound (adding another methyl group) is prepared as described in Step C.

STEP E:

2,2,2-Trifluoro-1-[2-fluoro-3-(N,N-dimethylamino)-5-(1-diethylether)]phenyl ethanone Title compound is prepared as described in Step B of Example 6 except for work-up procedure. After hydrolysis with 3N hydrochloric acid, tetrahydrofuran is removed under reduced pressure and the aqueous solution is extracted twice with ethyl acetate, the aqueous medium is basified with a saturated sodium carbonate solution and extracted twice with ethyl acetate. The organic layers are combined, washed with brine, dried over magnesium sulfate and concentrated. The crude product is dissolved in diethyl ether and treated with a saturated solution of hydrochloric acid in diethyl ether. The hydrochloride salt is filtered and recrystallized from isopropanol-diethyl ether. The resulting salt is dissolved in water and treated with a saturated sodium carbonate solution. The resulting aqueous medium is extracted with ethyl acetate. The ethyl acetate solution is washed with brine, dried over magnesium sulfate and concentrated to afford title compound.

It is now established that Alzheimer's disease and other senile degenerative diseases such as senile dementia are characterized by a selective loss in the cerebral cortex of choline acetyltransferase, the enzyme responsible for the biosynthesis of acetylcholine. There also exists a good correlation between memory impairment or dementia and the decrement in cholinergic transmission. Thus, impaired cholinergic transmission in the central nervous system may be, at least in part, responsible for the symptomatology of Alzheimer's disease and senile dementia. In support to these conclusions such compounds as physostigmine and 1,2,3,4-tetrahydro-9-aminoacridine (THA), compounds which prevent the catabolism of acetylcholine have found a place in the treatment of Alzheimer's and other senile degenerative diseases. Indeed, it has been recognized that the extent of improvement of cognitive functions has been closely related to the degree of inhibition of acetylcholinesterase.

The compounds of the present invention are useful in treating other conditions responsive to inhibition of acetylcholinesterase such as Myasthenia Gravis [*J. Neurol Neurosurg. Psychiatry*, 46 (10) 1983, 929–935, *Neurology* 42 (6) 1992, 1153–1156], antidotes against poisoning with organophosphates [see U.S. Pat. No. 5,171,750, *Int. J. Clin. Pharmacol. Ther. Toxicol.* 27 (8) 1989, 367–387], and glaucoma (*Arch. Clin. Exp. Ophthalmol.* 229 (3), 1991, 252–253)

The compounds of Formula I are pharmacologically active agents capable of inhibiting acetylcholinesterase as demonstrable in standard biological in vitro and in vivo test procedures. Indeed, based upon standard laboratory procedures, it is to be shown that the compounds of Formula I are potent and selective, quasi irreversible inhibitors of acetylcholinesterase capable of demonstrating advantages over the prior art, particularly physostigmine, in their use in the treatment of Alzheimer's disease and senile dementia. The compounds, in general, will exert their acetylcholinesterase inhibitory properties within the dose range of about 0.01 mg to 5 mg per kilogram of body weight for the preferred compounds.

For pharmacological end-use applications, the compounds of Formula I are preferentially administered in the form of their pharmaceutically acceptable acid addition salts. Of course, the effective dosage of the compounds will vary according to the individual potency of each compound employed, the severity and nature of the disease being treated and the particular subject being treated. In general, effective results can be achieved by administering a compound at a dosage of about 0.01 mg to about 20 mg per kilogram of body weight per day, administered systemically. Therapy should be initiated at lower dosages. The dosage thereafter may be administered orally in solid dosage forms, e.g., capsules, tablets, or powders, or in liquid forms, e.g., solutions or suspensions. The compounds may also be injected parenterally in the form of sterile solutions or suspensions.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula I compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula I compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the .other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

What is claimed is:

1. A method of treating degenerative dementias by administering to a patient in need of such therapy an effective amount of a compound of Formula I

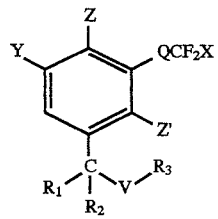

stereoisomers or pharmaceutically acceptable salts thereof, wherein each of Z and Z' are independently H or F;

Q is $$\overset{O}{\underset{}{\overset{\|}{C}}},$$

CH(OH), or $$\overset{O}{\underset{}{\overset{\|}{CHOCR_4}}};$$

X is H, Br, Cl, F or $CF_3$;

Y is H, Br, Cl, F, OH, $OR_5$, $OC(O)R_4$, $N_3$, CN, $NO_2$, $SO_3H$, $CO_2R_4$, $NH_2$, $NR_9R'_9$, $C(R_6)(R_7)(V'R_8)$ or $C(O)R_7$, provided that when both Z and Z' are F, then Y is H or F;

V and V' are each independently $CH_2$ or O;

$R_1$ is H or $CH_3$;

$R_2$, $R_9$ and $R'_9$ are each independently $(C_{1-6})$alkyl;

$R_3$, $R_6$, $R_7$ and $R_8$ are each independently H or $(C_{1-6})$alkyl, $(C_{3-6})$cycloalkyl;

or $R_2$ and V—$R_3$ taken together with the carbon atom to which they are attached form a 3–6 membered ring;

$R_4$ is H, $(C_{1-10})$alkyl, $(C_{0-4})$alkylene aryl or $(C_{3-8})$ cycloalkyl; and $R_5$ is $(C_{1-10})$alkyl, benzyl, phenethyl or $(C_{3-6})$cycloalkyl.

2. The method of claim 1 wherein Q is C(O).
3. The method of claim 1 wherein X is F.
4. The method of claim 1 wherein each of Z, Z' and Y are hydrogen.
5. The method of claim 1 wherein $R_1$, $R_2$, V and $R_3$ are respectively methyl, methyl, methylene and hydrogen.
6. The method of claim 1 wherein the compound is 2,2,2-Trifluoro-1-(3-tert-butyl)phenyl ethanone.
7. The method of claim 1 wherein the compound is 2,2,2-Trifluoro-1-(3-tert-butyl)phenyl ethanol.
8. The method of claim 1 wherein the compound is [2,2,2-Trifluoro-1-(3-tert-butyl)phenyl]ethyl acetate.
9. The method of claim 1 wherein the compound is 2,2,2-Trifluoro-1-[3-(2-propyl methyl ether)]phenyl ethanone.
10. The method of claim 1 wherein the compound is 2,2,2-Trifluoro-1-[3-(2-propanol)]phenyl ethanone.
11. The method of claim 1 wherein the compound is 2,2,2-Trifluoro-1-[2-fluoro-5-(1-diethylether)]phenyl ethanone.
12. The method of claim 1 wherein the compound is 2,2,2-Trifluoro-1-(2-fluoro-3-isopropyl)phenyl ethanone.
13. The method of claim 1 wherein the compound is 2,2,2-Trifluoro-1-[2-fluoro-3-(N,N-dimethylamino)-5-(1-diethylether)]phenyl ethanone.

* * * * *